United States Patent [19]

Weeks

[11] Patent Number: Plant 5,481

[45] Date of Patent: May 28, 1985

[54] ROSE PLANT

[76] Inventor: O. L. Weeks, 926 W. Philadelphia, Ontario, Calif. 91761

[21] Appl. No.: 540,413

[22] Filed: Oct. 11, 1983

[51] Int. Cl.[3] ..... A01H 5/00
[52] U.S. Cl. ..... Plt./19
[58] Field of Search ..... Plt./19

*Primary Examiner*—Robert E. Bagwill

*Attorney, Agent, or Firm*—Vincent G. Gioia

[57] ABSTRACT

The present invention relates to a new and distinct variety of rose plant of the hybrid tea rose class, which was originated by my crossing as seed parent the rose known as "Mr. Lincoln" (U.S. Plant Pat. No. 2,370) and as pollen parent, my seedling of ("Suspense"×"King's Ransom"). The denomination of this new rose is "Big Apple".

1 Drawing Figure

Among the novel characteristics possessed by this new variety which distinguish it from its parents and all other varieties of which I am aware are its large, well petaled, cardinal red flowers borne almost always one to a stem and with a pleasant old rose fragrance. The flowers open with high centers and remain attractive as large open blooms. The plant is vigorous and tall growing. Asexual reproduction by budding of the new variety as performed in San Bernardino County, Calif., shows that the foregoing and other distinguishing characteristics come true to form and are established and transmitted through succeeding propagations.

The new variety is brighter red than its seed parent with different bud form and larger petals. Also, foliage is lighter in color and larger than the seed parent and the plant, while well contained, is more spreading. The pollen parent seedling ("Suspense"×"King's Ranson") is an orange red bicolor. The growth habit and foliage of the new variety is superior to the pollen parent.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "60A" is plate 60A of The Royal Horticultural Society Colour Chart.

Parentage: Seedling.
*Seed parent.*—"Mr. Lincoln".
*Pollen parent.*—("Suspense"×"King's Ranson").
Class: Hybrid tea.

The following observations are made of specimens grown outdoors in San Bernardino County, Calif., during the month of August.

FLOWER

Blooming habit: Recurrent.
Bud:
(1) *Size.*—Medium to large.
(2) *Form.*—Long pointed.
(3) *Color.*—After sepals divide, buds are near 60A.
(4) *Sepals.*—Longer than bud, few appendages, foliated.

(5) *Peduncle.*—Length — medium. Aspect — heavily accented with small prickles. Strength — erect, strong. Color — near 143C.

Bloom:
(1) *Size.*—Average size when fully expanded — very large (about 5 to $5\frac{3}{4}$ inches).
(2) *Borne.*—Singly , one to a stem.
(3) *Form.*—High centered with slight indentation at crown as center starts to unfold, first petals reflex as buds unfurl but not as flower opens.
(4) *Petalage.*—Number of petals under normal conditions — about 30 to 35.
(5) *Color.*—As sepals break and separate, initial coloring visible is a red-purple near 60A. When sepals fall and petals begin to unfurl, petal undersurface appears more blood red 45D. However, petals reflex quickly and deeper red tone, currant red 47A, of petal top surface is quickly seen. Contrast in red tones between petal top surface and undersurface becomes more apparent at the $\frac{1}{3}$ to $\frac{1}{2}$ open stages but diminishes as bloom opens further. At fully open stage flower coloring appears more uniform, cardinal red 53B with 53D highlights.

Petals:
(1) *Texture.*—Thick and heavy.
(2) *Appearance.*—Inside and outside velvety.
(3) *Form.*—Ovate with rounded tip.
(4) *Arrangement.*—Regularly arranged.
(5) *Petaloids in Center.*—Few.
(6) *Persistence.*—Retains a few petals.
(7) *Fragrance.*—Pleasant, old rose.
(8) *Lasting quality.*—Long lasting quality on plant and 3 to 4 days as cut flower.

REPRODUCTIVE ORGANS

Stamens, filaments and anthers:
*Arrangement and color.*—Reddish yellow stamens regularly arranged around styles with light yellow anthers.
Pollen:
*Color.*—Light yellow.
Styles: Bunched, uneven length, some tall.
Stigmas:
*Color.*—Light yellow.
Hips: None observed.

PLANT

Form: Upright, moderately spreading, neatly compact.
Growth: Very vigorous.
*Height attained.*—About 5 feet.
Foliage: Compound 5 leaflets.
(1) *Size.*—Medium to large.
(2) *Quantity.*—Abundant, covers plant.
(3) *Color.*—New foliage: Upper side — reddish green Under side — reddish green with bronze overlay Old foliage: Upper side — near 147B Under side — near to 147B
(4) *Shape.*—Oval, long, pointed.
(5) *Texture.*—Upper side is waxy and under side is dull.
(6) *Edge.*—Serrate.
(7) *Serration.*—Small, light.
(8) *Leaf stem.*—Color — near to 147B to C. Under side — near 147B to C.
(9) *Stipules.*—Bearded, medium length.
(10) *Resistance to disease.*—Mildew — average.

Wood:
(1) *New wood.*—Color — near 147B. Bark — smooth.
(2) *Old wood.*—*Color* — *near* 147B. Bark — smooth.
Thorns:
(1) *Thorns.*—Quantity (main stalk) — many. On laterals from stalk — many. Form — thin, pointed sharply downward. Length — small to medium. Color — near 147C. Position — irregular.
(2) *Prickles.*—Profuse.
Winter hardiness: Needs winter protection in severe climate.

I claim:

1. A new and distinct variety of rose plant of the hybrid tea rose class, substantially as shown and described, characterized particularly by large, well petaled cardinal red flowers borne one to a stem on a vigorous plant.

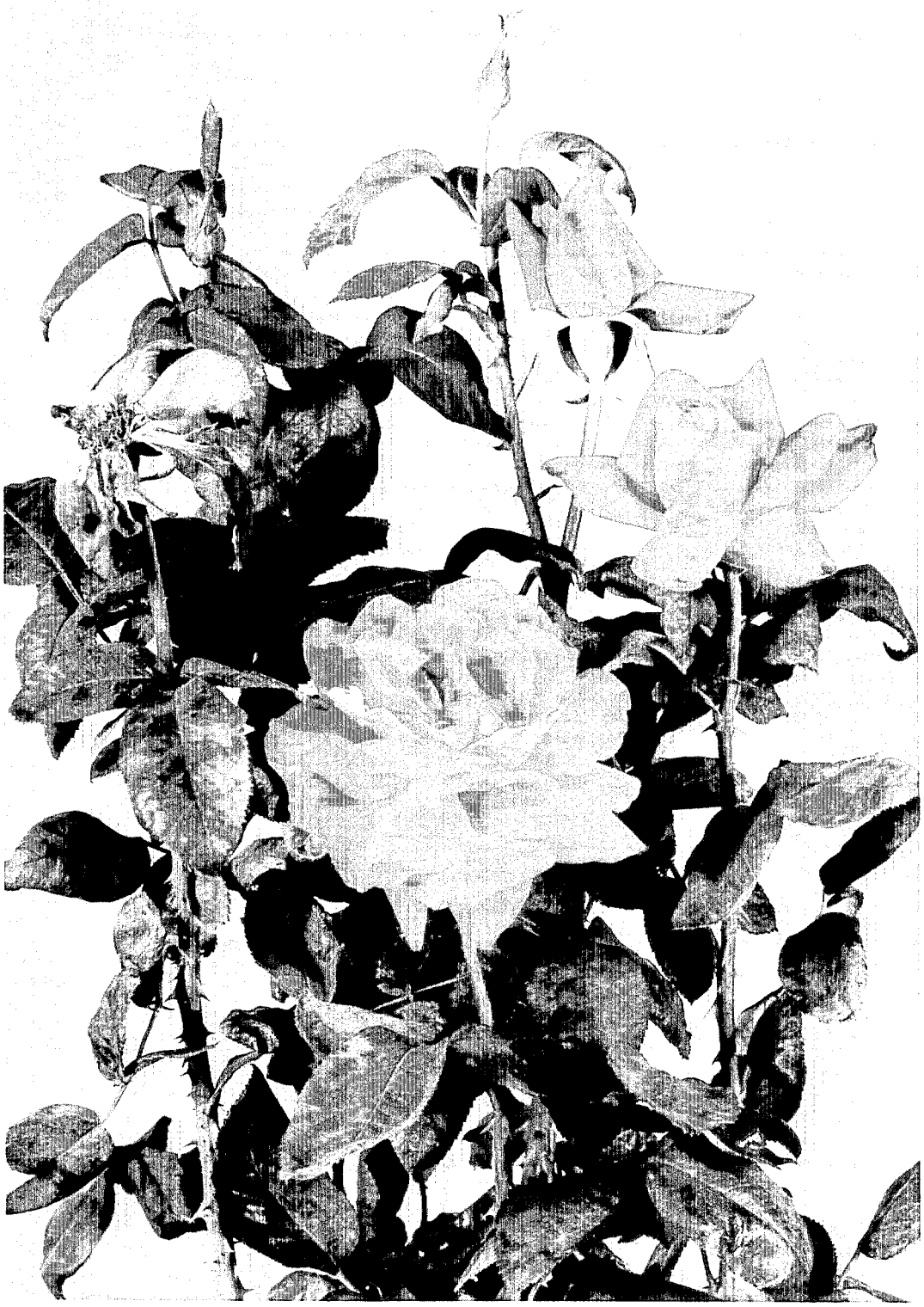

* * * * *